(12) United States Patent
Hazlebeck et al.

(10) Patent No.: US 10,907,127 B2
(45) Date of Patent: Feb. 2, 2021

(54) ALGAE CULTIVATION SYSTEMS AND METHODS WITH BORE WAVES

(71) Applicant: Global Algae Innovations, Inc., San Diego, CA (US)

(72) Inventors: David A. Hazlebeck, El Cajon, CA (US); Rodney Corpuz, Lihue, HI (US)

(73) Assignee: Global Algae Technology, LLC, Santee, CA (US)

( * ) Notice: Subject to any disclaimer, the term of this patent is extended or adjusted under 35 U.S.C. 154(b) by 376 days.

(21) Appl. No.: 15/590,403

(22) Filed: May 9, 2017

(65) Prior Publication Data

US 2017/0318771 A1 Nov. 9, 2017

Related U.S. Application Data

(60) Provisional application No. 62/333,724, filed on May 9, 2016, provisional application No. 62/333,709, filed on May 9, 2016.

(51) Int. Cl.

| | |
|---|---|
| *A01H 13/00* | (2006.01) |
| *C12M 1/34* | (2006.01) |
| *A01G 33/00* | (2006.01) |
| *C12M 1/00* | (2006.01) |

(52) U.S. Cl.
CPC .............. *C12M 41/34* (2013.01); *A01G 33/00* (2013.01); *C12M 21/02* (2013.01); *C12M 23/18* (2013.01); *C12M 23/28* (2013.01); *Y02A 40/80* (2018.01); *Y02E 10/20* (2013.01); *Y02E 10/30* (2013.01); *Y02E 60/16* (2013.01)

(58) Field of Classification Search
CPC ....... A01G 33/00; C12M 21/02; C12M 23/18; C12M 1/42; C12M 29/12; C12M 35/04; C12M 41/34; A01H 4/001; C12N 1/12
USPC .......................................................... 47/1.4
See application file for complete search history.

(56) References Cited

U.S. PATENT DOCUMENTS

| | | | |
|---|---|---|---|
| 2,732,662 A | 1/1956 | Myers et al. | |
| 3,243,918 A | 4/1966 | Machiedo et al. | |
| 3,462,360 A * | 8/1969 | McKinney | C02F 3/1257 210/195.3 |
| 4,253,271 A | 3/1981 | Raymond | |
| 4,320,594 A | 3/1982 | Raymond | |
| 5,981,271 A | 11/1999 | Doucha et al. | |
| 8,398,296 B2 * | 3/2013 | Miller, III | B01F 13/0015 261/120 |
| 8,541,225 B2 | 9/2013 | Hazlebeck et al. | |
| 8,748,162 B2 | 6/2014 | Hazlebeck et al. | |
| 8,752,329 B2 | 6/2014 | Parsheh et al. | |
| 2008/0155890 A1 * | 7/2008 | Oyler | A01G 22/00 47/1.4 |

(Continued)

OTHER PUBLICATIONS

Dodd, "Elements of Pond Design and Construction," CRC Handbook of Microalgal Mass Culture, CRC Press 1986, pp. 265-283.

(Continued)

*Primary Examiner* — Christopher D Hutchens
(74) *Attorney, Agent, or Firm* — Quarles & Brady LLP

(57) ABSTRACT

An algae cultivation system includes generating a translating hydraulic jump wave that travels across a gas-liquid interface of an algae cultivation fluid contained in the algae cultivation system. The translating hydraulic jump wave has Froude number greater than 1.

62 Claims, 18 Drawing Sheets

(56) References Cited

U.S. PATENT DOCUMENTS

| | | | |
|---|---|---|---|
| 2010/0147332 A1* | 6/2010 | Rhyne | F16L 55/24 134/22.12 |
| 2010/0325948 A1* | 12/2010 | Parsheh | A01G 33/00 47/1.4 |
| 2011/0229775 A1 | 9/2011 | Michaels et al. | |
| 2011/0287531 A1 | 11/2011 | Hazlebeck | |
| 2012/0117869 A1* | 5/2012 | Javan | A01G 33/00 47/60 |
| 2012/0228398 A1* | 9/2012 | Foglizzo | B05B 17/08 239/17 |
| 2012/0272574 A1* | 11/2012 | Parsheh | A01G 33/00 47/62 R |
| 2013/0109008 A1* | 5/2013 | Stammbach | C12M 21/02 435/3 |
| 2013/0269244 A1* | 10/2013 | Jovine | A01G 33/00 47/1.4 |
| 2014/0105685 A1* | 4/2014 | McFarland | E04H 4/0006 405/79 |
| 2014/0250579 A1* | 9/2014 | Slater | A63B 69/0093 4/491 |
| 2014/0322805 A1* | 10/2014 | Hazlebeck | C12M 29/12 435/292.1 |
| 2014/0329297 A1* | 11/2014 | Longan | C12M 21/02 435/252.1 |
| 2015/0182923 A1* | 7/2015 | Malkiel | B01F 3/04765 366/279 |
| 2017/0027120 A1* | 2/2017 | Parsheh | A01G 33/00 |
| 2017/0044478 A1* | 2/2017 | Downey | A01G 33/00 |

OTHER PUBLICATIONS

Chiaramonti et al., "Review of Energy Balance in Raceway Ponds for Microalgae Cultivation: Re-Thinking a Traditional System is Possible," Applied Energy 102, 2013, pp. 101-111.

* cited by examiner

ALGAE CULTIVATION SYSTEMS AND METHODS WITH BORE WAVES

CROSS-REFERENCE TO RELATED APPLICATION(S)

This application claims priority to U.S. provisional application Nos. 62/333,709, and 62/333,724, filed on May 9, 2016, each of which is incorporated by reference herein and relied upon in its entirety.

STATEMENT OF FEDERALLY SPONSORED RESEARCH OR DEVELOPMENT

This invention was made with government support under award #DE-EE0006314 and award #DE-EE0007689, both awarded by the Department of Energy ("DOE"), and under sub-recipient #06-S140633 of prime award #W911NF-14-2-0017 awarded by the Defense Advanced Research Projects Agency ("DARPA"). The government has certain rights in the invention.

BACKGROUND OF THE DISCLOSURE

The present disclosure relates generally to algae cultivation systems and methods, and more particularly to algae cultivation systems and methods that provide higher algae production outputs and lower operating and capital costs.

Algae cultivation has become widely recognized as a promising source of food, biofuel, chemicals, and nutraceuticals. An enduring obstacle to economical algae production has been the inability to attain high productivity in a low cost cultivation system that is scalable to farms with hundreds to thousands of acres of algae. Closed photobioreactors typically achieve a high productivity by utilizing short light path and environmental controls, but most closed photobioreactors have high capital and operating costs, and are not scalable. Open cultivation systems have lower capital and operating costs, but typically exhibit a lower productivity than closed photobioreactors. Most open cultivation systems are based on high-rate raceway ponds. In these conventional raceways, the typical operating depth is 20 to 30 cm, the typical fluid velocity is 10 cm/s to 30 cm/s, and the individual raceways scale only to a few acres.

Other less conventional algae cultivations systems attain higher productivity by utilizing a sloped bottom to attain shallower operating depths and using various mixing features to attain better mixing.

Very shallow cultivation systems (i.e., with depths of 0.5 to 5 cm) require an engineered smooth surface (e.g., concrete or other solid materials) and a high slope (i.e., of 1% or greater). And algae cultivation systems that use improved mixing techniques in an attempt to attain higher productivity suffer from extremely high capital and operating costs because of the need for engineered smooth surfaces and high slopes, which require very high levels of pumping energy.

One less conventional algae cultivation system includes a lined raceway without an engineered smooth surface has a shallow depth of 7.5 cm to 15 cm, which is about one half to one third the depth of more conventional raceways. This system offers capital and operating costs similar to conventional raceways, is more scalable than conventional raceways, and attains higher productivity. But a further reduction in depth to this system cannot be attained because of grading tolerances, natural variations, and ground settling in earthen raceways having plastic liner results in depth variations in the range of 2 cm to 6 cm.

Another algae cultivation system includes a similar slope having small steps, waterfalls, or other uneven elements to disturb the surface and enhance gas transfer. But the depth in this system is also limited by the energy required for pumping if the slope is too great. Attaining better mixing through typical raceway velocities up to 30 cm/s would require a slope with a gradient of ~0.1%.

It should be appreciated from the foregoing, that new and improved algae cultivation systems and methods are needed.

SUMMARY OF THE DISCLOSURE

The present disclosure provides algae cultivation systems and methods that can enhance algal growth circulation through periodic generation of one or more waves that move fluid through the cultivation systems such that a translating hydraulic jump is generated at the wave front, herein referred to as a translating hydraulic jump wave or bore wave. The bore waves can form undular bores where the leading wave front is followed by a series of well-developed undulations. The waves generate highly turbulent mixing with extensive vertical mixing that persists well after the wave passes. As a result, the algae cultivation systems and methods of the present disclosure can achieve good mixing, independent of base fluid flow turbulence. Shallow algae cultivation systems can also be attained and operated without the need for high slopes, or the need for active mixers to induce intensive turbulence.

The bore waves can be supercritical, so that downstream objects do not cause a change in flow direction. The bore waves can also flow over irregularities, even if the irregularities are on the same order as the depth of the cultivation system. Thus, flow throughout the algae cultivation systems of the present disclosure (e.g., flow through shallow raceway systems) can be maintained without the expense of tight engineering tolerances.

The base flow rate in the algae cultivation systems herein can also be slower, and the bore waves can be periodically induced to provide lower overall operational energy usage relative to typical continuous flow algae cultivation systems having a velocity that is high enough to achieve turbulent mixing. Because the bore waves can be periodically introduced, the overall mixing rate in the algae cultivation systems and methods can easily be varied throughout the day, providing greater mixing when the most sunlight is available for algae growth.

The algae cultivation systems and methods herein can have a level bottom, a downward-sloped bottom, or an upward-sloped bottom, and can include open or covered raceways or closed horizontal photobioreactors with an air-gap between the cultivation media and the top of the photobioreactor. As will be appreciated, each of the cultivation systems and methods described herein contain an algae cultivation fluid with a surface having a gas-liquid interface across which the bore or translating hydraulic jump waves travel.

As will be appreciated, the translating hydraulic jump or bore waves can be generated utilizing a variety of different techniques or mechanisms. In one aspect, a fluid level in a portion of the algae cultivation system is increased relative to a base fluid level such that supercritical flow is induced. In another aspect, the fluid in a deeper section of the cultivation system is accelerated mechanically instead of accelerated only via the use of gravity. Other non-limiting examples of methods and mechanisms for creating a fluid level difference and accelerating fluid flow to generate the translating hydraulic jump waves include rapidly pushing fluid into a portion of the cultivation system using a pumping device having a variable speed drive, mechanically pushing fluid forward or backward in a portion of a cultivation system raceway, rapidly stopping the flow in a portion of cultivation system raceway such that the fluid level rises quickly and a back wave is created, rapidly releasing fluid from a catch basin that is deep enough relative to the base level of the cultivation system to create a bore wave, and rapidly lifting the bottom of a cultivation system to cause fluid to accelerate and create a bore wave.

In one particular aspect of the present disclosure, a translating hydraulic jump wave having a Froude number greater than 1 is generated that travels across a gas-liquid interface of an algae cultivation fluid contained in an algae cultivation system.

In another aspect, the translating hydraulic jump wave has Froude number greater than 1.3.

In yet another aspect, the translating hydraulic jump wave includes a ratio of the wave depth to algae cultivation fluid depth that is greater than 1.15.

In still another aspect, the translating hydraulic jump wave includes a ratio of wave depth to algae cultivation fluid depth that is at least 1.4.

In other aspects, the translating hydraulic jump wave includes a velocity of (i) greater than 40 cm/s relative to a velocity of the algae cultivation fluid, or (ii) greater than 70 cm/s relative to a velocity of the algae cultivation fluid.

It is an objective of the present disclosure to attain higher productivity in algae cultivation using wave flow as a primary mode of fluid movement.

It is a further objective to reduce the increase in energy use for cultivation fluid circulation in algae cultivation systems.

It is a further objective to reduce the cultivation fluid velocity required for mixing in algae cultivation systems.

It is a further objective to reduce the slope required to achieve adequate mixing in sloped algae cultivation systems.

It is a further objective to utilize wave flow to attain shallow operating depths of 0.5 to 6.5 cm in level algae cultivation systems.

It is a further objective to utilize wave flow to attain shallow operating depths of 0.5 to 6.5 cm in sloped algae cultivation systems with an upward or downward with gradient of less than 0.5% and preferably less than 0.1%.

It is a further objective to utilize wave flow to attain a shallow operating depth of 0.5 to 6.5 cm in algae cultivation systems formed by grading without addition of an engineered smooth surface.

It is a further objective to utilize wave flow to attain a shallow operating depth of 0.5 to 6.5 cm in algae cultivation systems with bottom irregularities of 0.5 cm or greater.

It is a further objective to utilize wave flow to achieve higher mixing and higher gas exchange in algae cultivation systems.

It is a further objective to utilize wave flow to reduce the capital and operating costs of shallow algae cultivation systems.

DETAILED DESCRIPTION

Figure 1:
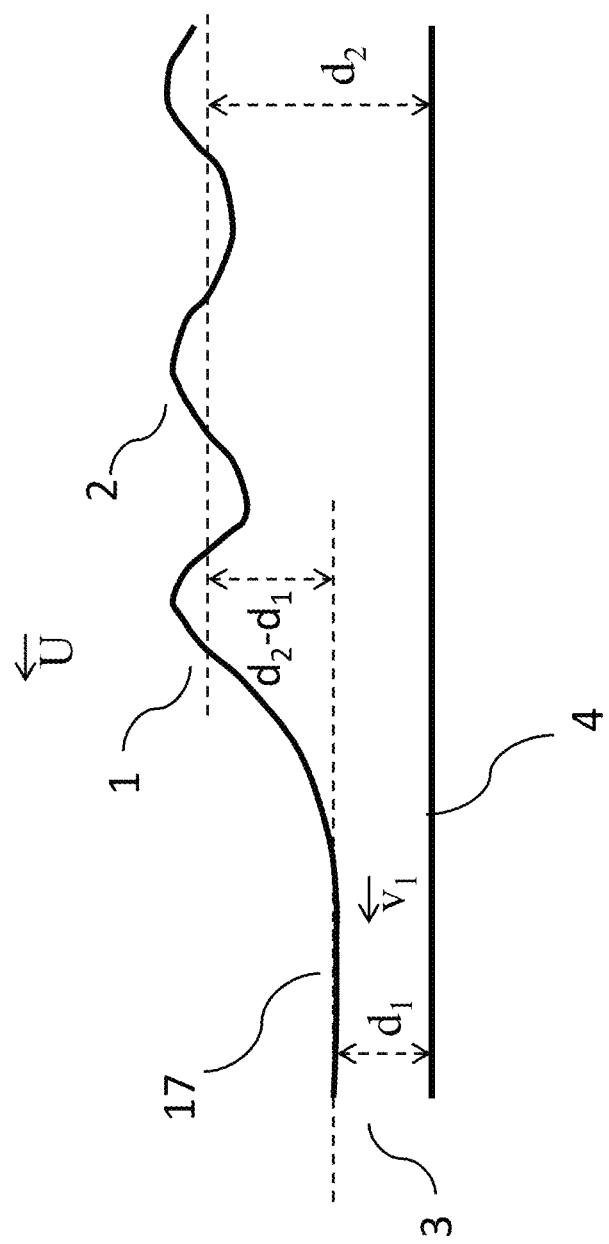
FIG. 1 is a cross-sectional view illustrating an undulated bore or translating jump wave travelling in an algae cultivation system according to one embodiment of the present disclosure.

Referring now to the figures, FIG. 1 is a cross-sectional view illustrating an undulated bore or translating hydraulic jump wave traveling in any one of the algae cultivation systems or methods of the present disclosure. An initial hydraulic jump or bore wave 1 travels from right to left at a bore wave velocity U, and a bore wave depth of $d_2$. A second wave or undulation 2 follows the initial wave. The bore wave 1 moves into or through an algae cultivation fluid 3. Cultivation fluid 3 includes a gas-liquid interface 17 on a surface of the fluid 3, a cultivation fluid velocity $v_1$, and a cultivation fluid depth $d_1$. The algae cultivation system further includes a bottom 4, which in the embodiment of FIG. 1 is shown as level, but can be sloped upwardly or downwardly relative to the direction of wave flow. The bore or translating hydraulic jump wave velocity U is the velocity of the bore wave relative to a fixed point in the algae cultivation system, which is positive in the direction in which the wave translates. The algae cultivation fluid velocity $v_1$ is the velocity of the algae cultivation fluid downstream from the bore wave relative to a fixed point in the cultivation system. The fluid velocity $v_1$ is positive if the fluid is moving in the same direction as the bore wave, and negative if the fluid is moving in the opposite direction of the bore wave.

The Froude number for the bore wave is $$\frac{U - v_1}{\sqrt{g\,d_1}};$$

where U is the bore wave velocity, $v_1$ is the cultivation fluid velocity downstream of the bore wave, $U-v_1$ is the bore wave velocity relative to the cultivation fluid velocity, g is acceleration due to gravity, and $d_1$ is the depth of the algae cultivation fluid downstream of the bore wave. The bore waves contemplated herein can be supercritical and have a Froude number greater than 1. In certain embodiments, the bore waves can have a Froude number greater than 1.3, which ensures that the initial wave is a breaking wave. For a depth $d_1$ between of 1 cm and 6.5 cm downstream of the bore wave, a Froude number greater than 1.3 corresponds to a minimum velocity for the wave relative to the algae cultivation fluid velocity, $U-v_1$, of 40 cm/s to 100 m/s. The wave fluid flux is the bore wave speed multiplied by the bore wave height, $d_2-d_1$. For a bore wave height of 1 cm or greater and a cultivation fluid velocity of 5 cm/s to 15 cm/s, the wave fluid flux is 45 cm$^2$/s to 105 cm$^2$/s. If friction over the distance of the translating hydraulic jump is neglected, then the depth ratio of the bore wave relative to the downstream depth, $d_2/d_1$, is greater than 1.15, which provides a 10% margin on maintaining a Froude number greater than 1. The depth ratio, $d_2/d_1$, in certain embodiments can be greater than 1.4 to attain a Froude number greater than 1.3.

Figure 2:
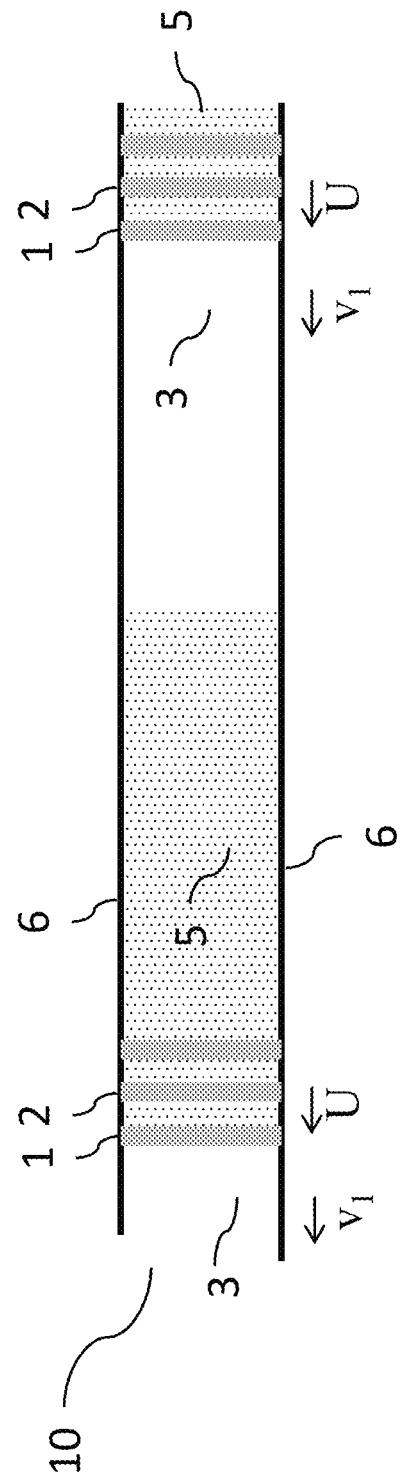
FIG. 2 is a plan view illustrating undulated bore or translating jump waves traveling in an algae cultivation system according to one embodiment of the present disclosure.

FIG. 2 is a plan view illustrating undulated bore waves traveling in one non-limiting embodiment of an algae cultivation system of the present disclosure. The fluid in the cultivation system of FIG. 2 is contained within a channel 10, and the initial translating hydraulic jump or bore wave 1 generated by the system travels from right to left at a bore wave velocity U. The second wave or undulation 2 follows the initial wave. The algae cultivation fluid 3 downstream of the initial bore wave 1 moves at a cultivation fluid velocity $v_1$, which may be in the same direction or in the opposite direction as the direction the bore wave moves. The algae cultivation fluid 5 upstream of the initial bore wave 1 is highly turbulent with good vertical mixing components. As will be appreciated, the bore wave in the system of FIG. 2 can be generated with any suitable wave generators discussed herein, and can be utilized in any of the algae cultivation systems and methods described herein.

Figure 3:
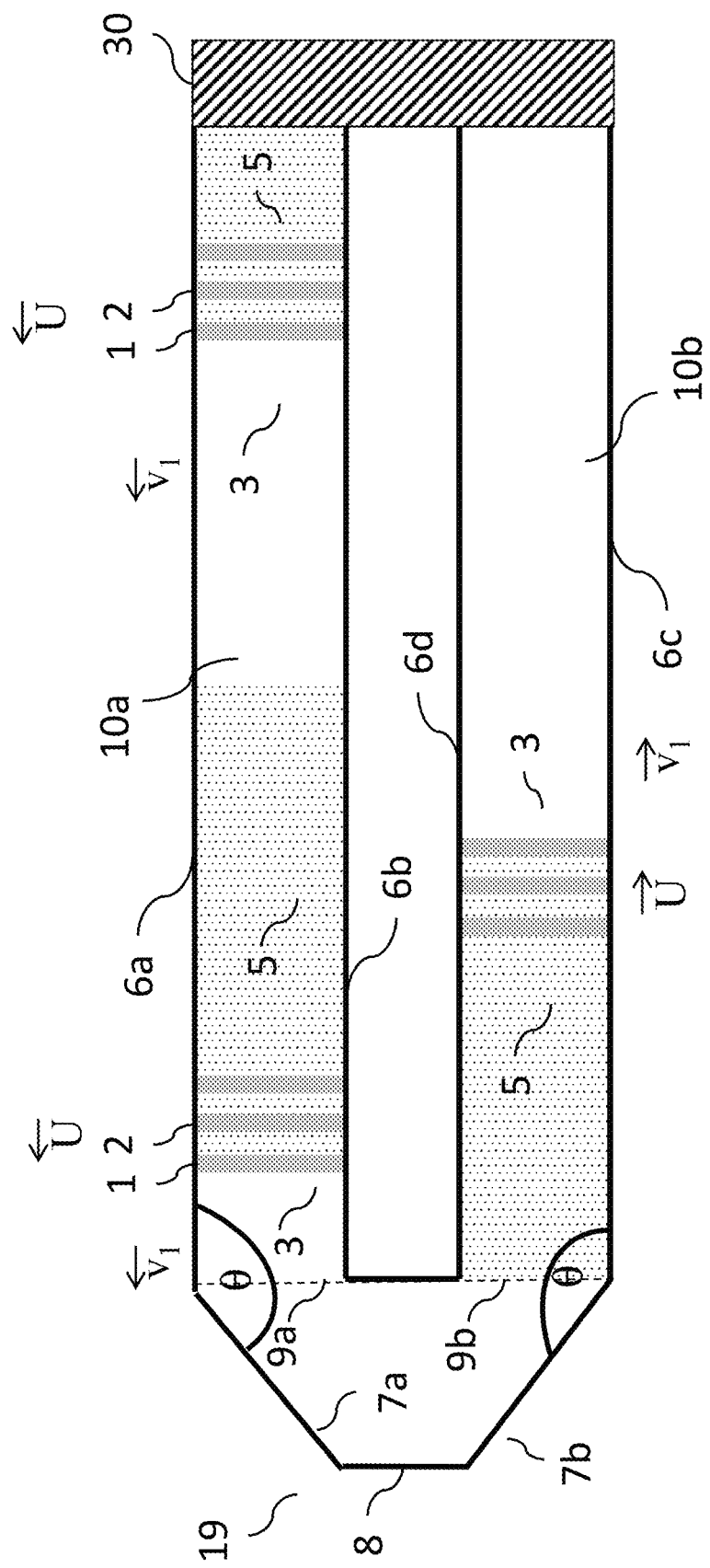
FIG. 3 is a plan view illustrating undulated bore or translating jump waves travelling in an algae cultivation system having two straight channels according to one embodiment of the present disclosure.

FIG. 3 is a plan view illustrating three undulated translating hydraulic jump or bore waves traveling in another non-limiting embodiment of an algae cultivation system of the present disclosure. The algae cultivation system of FIG. 3 includes two straight channels 10a and 10b in which algae cultivation fluid 3 is contained. Channel 10a includes a straight outer sidewall 6a and a straight inner sidewall 6b. Outer and inner sidewalls 6a, 6b are coterminous at an end portion 9a, which is shown by the dashed line in FIG. 3. Channel 10b likewise includes a straight outer sidewall 6c and a straight inner sidewall 6d. Outer and inner sidewalls 6c, 6d are coterminous at an end portion 9b, which is shown by dashed line 9b. Each end portion 9a, 9b extends perpendicular to the respective sidewall 6a, 6b. Channels 10a, 10b, are connected at one end by a bend 19 having angled sidewalls 7a, 7b. Sidewalls 7a, 7b each extend from their respective straight outer sidewalls 6a, 6c of the first and second channels 10a, 10b at an angle Θ relative to the respective sidewall 6a,6c such that no waves are reflected back up the channel 10a. It should be appreciated that while angled sidewalls 7a, 7b do not need to be straight, the angles Θ relative to the straight outer sidewalls 6a, 6c should be at least 135 degrees to prevent waves from reflecting back up the channel 10a. To put it another way, the angles relative to the end portions 9a, 9b should be greater than 45 degrees. Sidewalls 7a, 7b can be directly connected to each other, or connected via a straight end wall 8, which, as illustrated, is perpendicular to the inner and outer sidewalls of the channels 10a, 10b. At the other end of the system, channels 10a, 10b are connected by a translating hydraulic jump or bore wave generator 30. Wave generator 30 is configured to generate translating hydraulic jump waves that travel across the gas-liquid interface of the algae cultivation fluid contained in the system. An initial hydraulic jump or bore wave 1 that is generated by wave generator 30 travels from right to left at a velocity U in channel 10a, and from left to right at a velocity U in channel 10b. A second wave or undulation 2 follows the initial wave 1. The algae cultivation fluid 3 downstream of the bore wave 1 moves at a velocity v1, which may be in the same direction or the opposite direction of the movement of the bore wave. The fluid 5 upstream of the initial bore wave 1 is highly turbulent with strong vertical mixing. The wave generator 30 is configured to remove fluid from the channel 10b, and utilize that removed fluid to initiate or generate the translating hydraulic jump wave 1 travelling within channel 10a.

Figure 4:
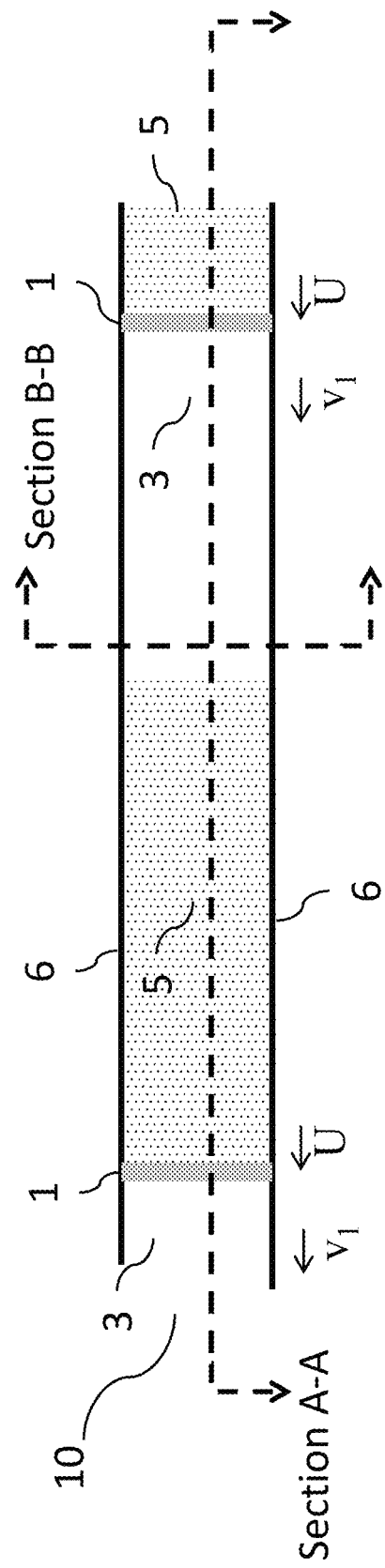
FIG. 4 is a plan view illustrating bore or translating jump waves travelling in an earthen lined algae cultivation system according to one embodiment of the present disclosure.
Figure 5:
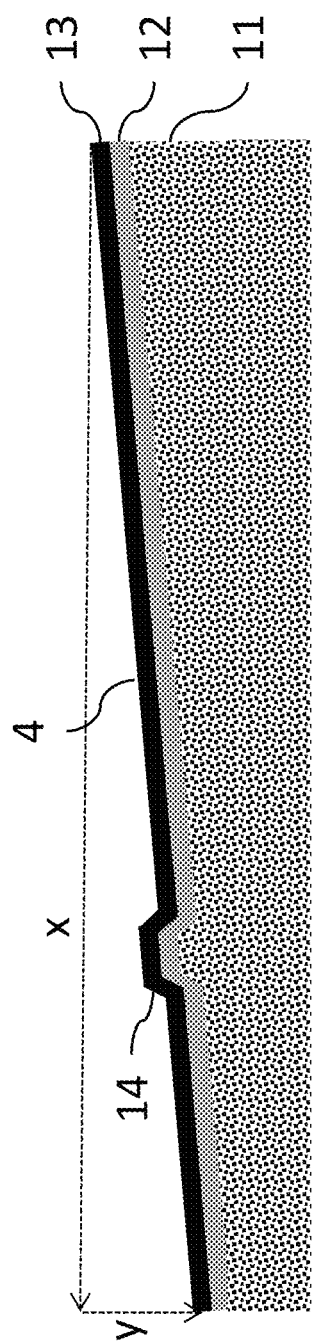
FIG. 5 is a cross-sectional view taken along lines A-A in FIG. 4
Figure 6:
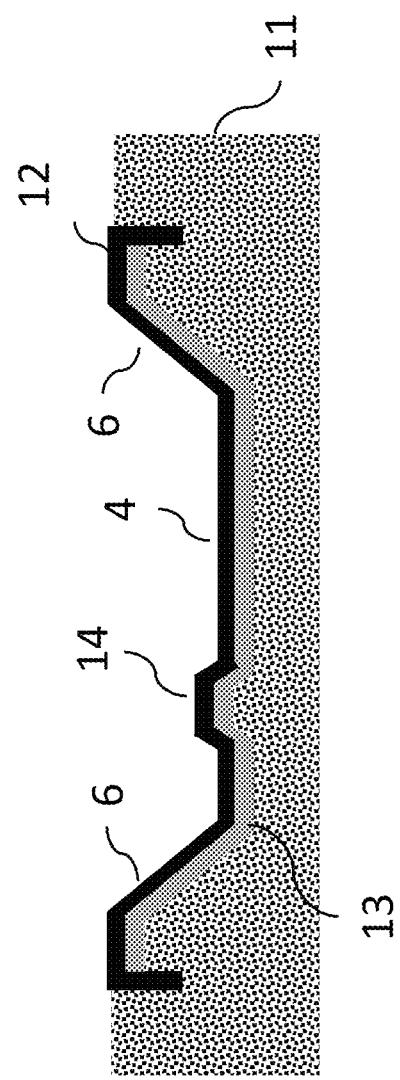
FIG. 6 is a cross-sectional view taken along lines B-B in FIG. 4.

FIGS. 4, 5 and 6 illustrate another non-limiting embodiment of an algae cultivation system of the present disclosure in which bore or translating hydraulic jump waves are generated in an earthen lined channel. FIG. 4 is a plan view of the system, while FIGS. 5 and 6 are parallel and perpendicular cross-sectional views of FIG. 4. The system of FIG. 4 includes a channel 10, which contains the algae cultivation fluid. Channel 10 can be formed by grading dirt 11 to form earthen sidewalls 6 and earthen bottom 4. The channel 10 is covered with an underlayment 12 and a liner 13, which is impermeable to the aqueous algae cultivation fluid. Liner 13 in an embodiment is comprised of plastic. The ground can be graded such that the bottom 4 of channel 10 is sloped downwardly, upwardly or not sloped at all (i.e., level). The slope can be defined as y/x, where y is vertical and x is horizontal. A bore wave 1, which can be generated by any suitable bore wave generator discussed herein, travels along the channel 10 at a bore wave speed U. The bottom 4 of channel 10 includes an irregularity 14. Irregularity is illustrated as a protrusion, but earthen lined channels can also have irregularities in the form of indentations, elevated regions, or dips with heights or depth changes ranging from 0.5 cm to 6 cm. Over time, soil and rocks in the earth shift, creating more irregularities in earthen algae cultivation systems. Fluid flow in earthen lined systems is typically subcritical with a Froude number of less than 1, so downstream irregularities can affect upstream flow. Irregularities can therefore have a significant impact on the flow pattern in these systems, and can create dry areas in which the cultivation fluid will flow around the irregularity if the system operating depth is less than 7.5 cm. To accommodate these irregularities, typical earthen raceways have cultivation depths of 10 cm to 30 cm, while shallow, sloped earthen raceways have depths of 7.5 cm to 15 cm. The algae cultivation systems of the present disclosure, on the other hand, utilize a translating hydraulic jump or bore wave 1 with a Froude number greater than 1, so that any downstream irregularities in the system do not impact upstream flow. That is, the generated bore wave 1 will flow over any irregularities rather than around them, which allows open raceway or lined earthen systems of the present disclosure to operate with raceways or channels having very shallow depths and slopes (e.g., depths of 0.5 cm to 6.5 cm, and slopes, y/x, between 0.5% and −0.5%, and in some embodiments between 0.1% and −0.1%).

Figure 7:
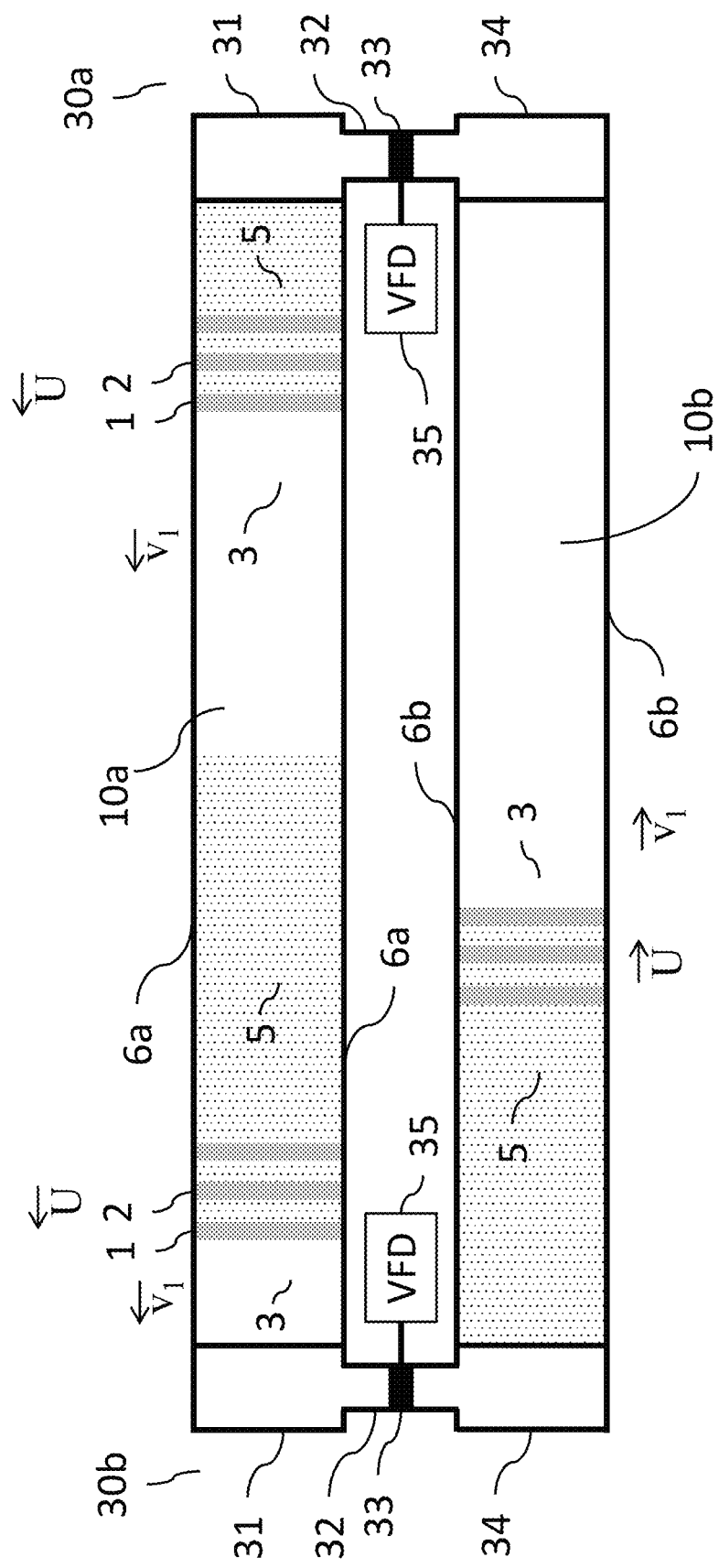
FIG. 7 is a plan view illustrating undulated bore or translating jump waves travelling in an algae cultivation system having a variable flow translating hydraulic jump wave generator according to one embodiment of the present disclosure.

FIG. 7 illustrates another non-limiting embodiment of an algae cultivation system of the present disclosure having a hydraulic jump wave generator. In particular, the system of FIG. 7 includes two bore wave generators 30a, 30b that generate translating hydraulic jump or bore waves that travel in two channels 10a, 10b contain the algae cultivation fluid. Each wave generator 30a, 30b includes a fluid pump 33 located at an entrance of the respective channel 10a, 10b. Algae cultivation fluid 3 exits each channel 10a, 10b and is collected at respective sump 31. Each sump 31 is connected via conduit 32 to another sump 34 located at an inlet of a respective channel 10a, 10b. The wave generators 30a, 30b each include a variable frequency drive 35 that controls the speed of the propeller pumps 33 to move the algae cultivation fluid 3 from the exits of sumps 31, to the entrance of sump 34 via the conduit 32. Bore or translating hydraulic jump waves 1 are formed by cycling the pump flow via the variable frequency drives 35 between a low volumetric flow and a high volumetric flow in which the high volumetric flow is at least two times the low volumetric flow. While the system of FIG. 7 illustrates a propeller pump, any suitable type of fluid pump capable of operating with variable flow can be used, including an Archimedes screw pump, a centrifugal pump, or a paddle wheel. It should be appreciated that any of the other algae cultivation systems herein capable of utilizing a fluid pump for the wave generator can likewise include a propeller pump, an Archimedes screw pump, a centrifugal pump, a paddle wheel or any other suitable fluid pump. It should further be appreciated that while FIG. 7 illustrates a sump connected with another sump via a conduit, an ordinary skilled artisan would understand that the sumps and conduits are not required for the system of FIG. 7 to operate with bore waves. For example, the system of FIG. 7 could instead use channels that are shaped to match the entrance and exit of the variable flow fluid pump, eliminating the need for sumps.

Figure 8:
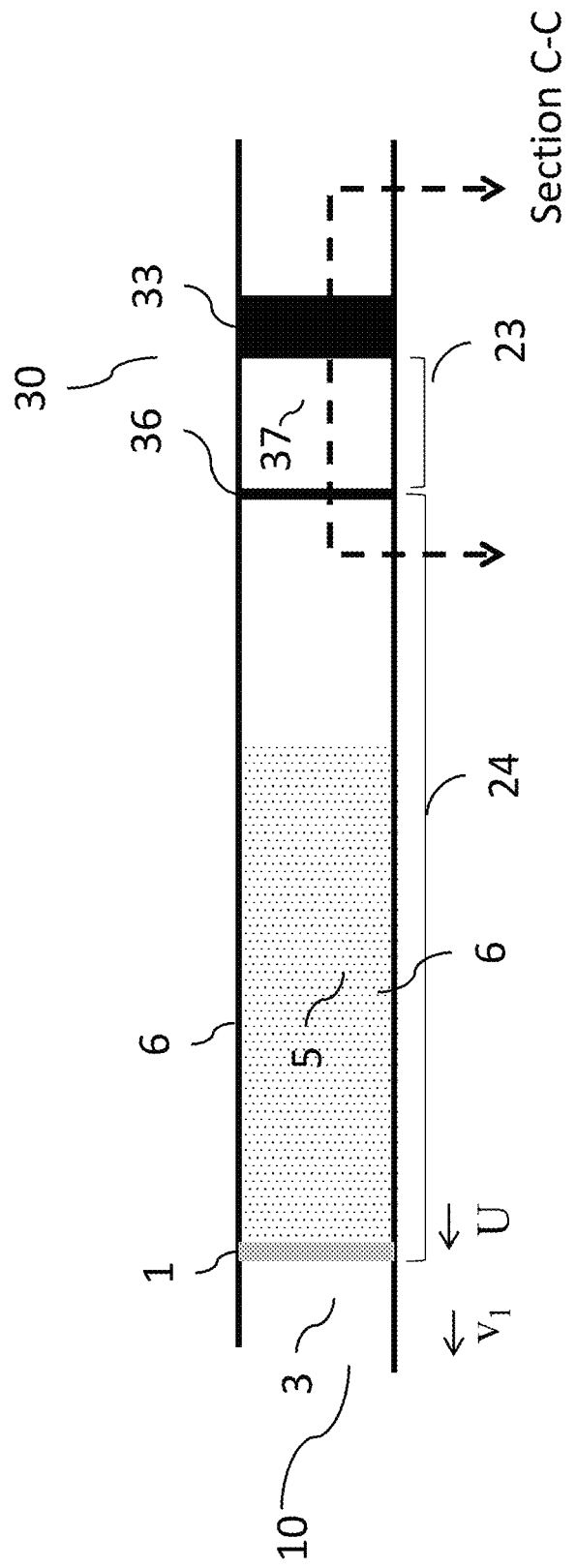
FIG. 8 is a plan view illustrating bore or translating jump waves travelling in an algae cultivation system having a translating hydraulic jump wave generator with a gate and fluid pump according to one embodiment of the present disclosure.
Figure 9:
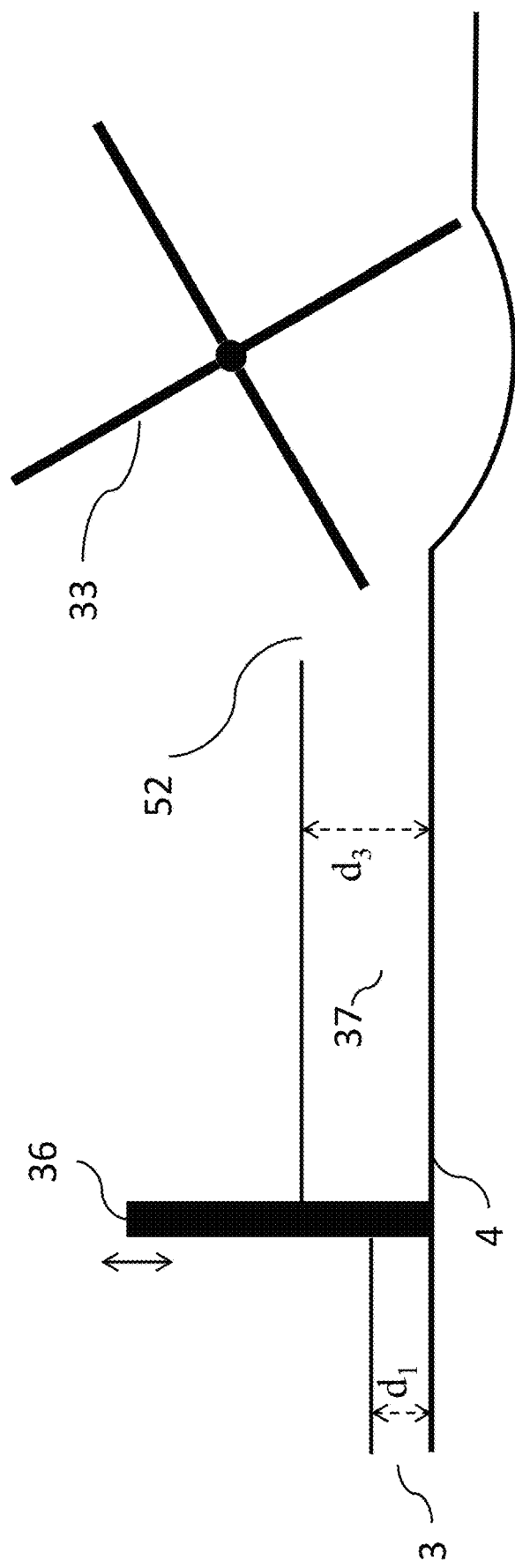
FIG. 9 is a cross-sectional view taken along lines C-C of FIG. 8.

FIGS. 8 and 9 illustrate another non-limiting embodiment of an algae cultivation system of the present disclosure in which a translating hydraulic jump wave generator 30 includes a gate 36 that opens to release fluid from a chamber 37 with a paddlewheel pump 33. FIG. 8 is a plan view of the system, while FIG. 9 is a cross-sectional view of the system. The system of FIGS. 8 and 9 include a channel 10 that contains the algae cultivation fluid. The channel 10 includes a first section 23 and a second section 24. The wave generator 30 includes the paddlewheel 33 and the chamber 37 formed within the first section 23 of the system or channel 10. The chamber 37 is defined by the gate 36, the channel sidewalls 6, the channel bottom 4 and the paddlewheel 33. The paddlewheel 33 operates continuously to move fluid into the chamber 37 through an outlet 52 of the paddlewheel. The movement of fluid into the chamber 37 increases the depth $d_3$ of the fluid in the chamber 37 to a level that is higher than the depth $d_1$ of cultivation fluid 3 in the second section 24 of the system or channel 10. As illustrated by the up and down arrows in FIG. 9, the gate 36 can be raised or lowered to either collect fluid in the chamber 37 or release fluid from the chamber 37 to the rest of the channel (i.e., the second section 24). When the gate 36 is raised, the fluid in the chamber 37 rapidly enters the channel 10, forming a translating hydraulic jump or bore wave 1 that travels down the channel away from the wave generator 30 at a bore wave velocity U. The cultivation fluid 3 in the channel 10 downstream of the bore wave travels at a velocity $v_1$, which can be an induced velocity created by the passing of the prior bore wave. In certain embodiments, instead of having a paddlewheel fluid pump, the fluid pump can be an Archimedes pump, a propeller pump or any other suitable fluid pump.

Figure 10:
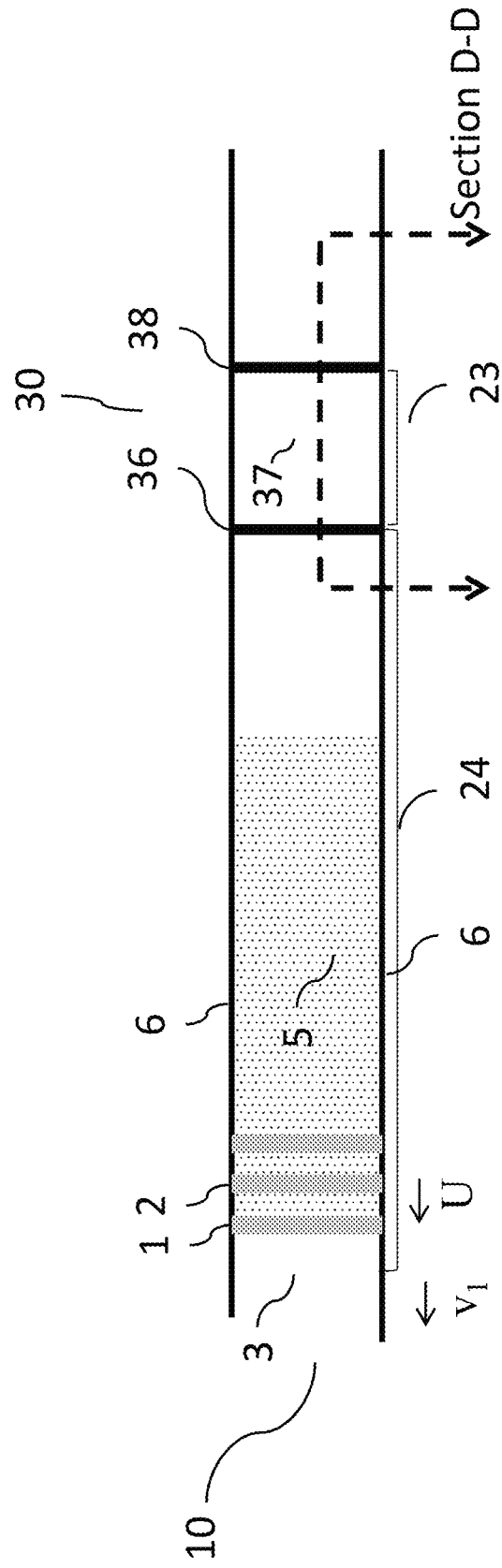
FIG. 10 is a plan view illustrating undulated bore or translating jump waves travelling in an algae cultivation system having a translating hydraulic jump wave generator having a gate and a step down according to one embodiment of the present disclosure.
Figure 11:
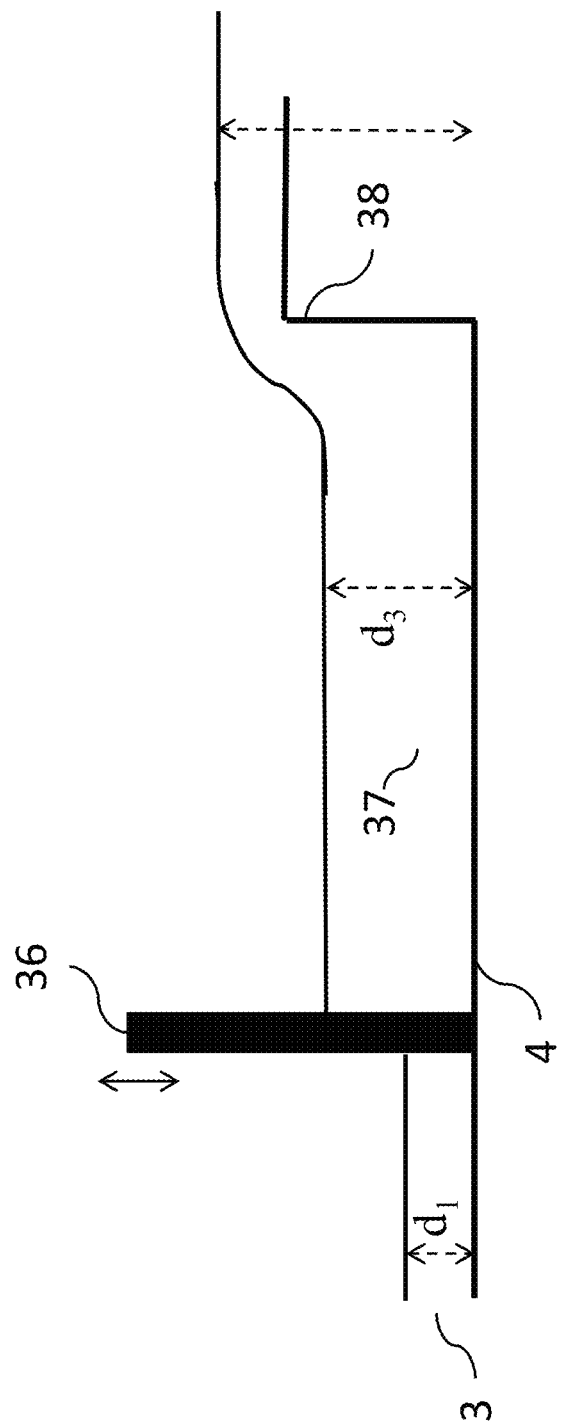
FIG. 11 is a cross-sectional view taken along lines D-D of FIG. 10.

FIGS. 10 and 11 illustrate another embodiment of an algae cultivation system of the present disclosure, which is similar to the system of FIGS. 8 and 9 including the bore wave generator 30 having a gate 36 that opens to release fluid from a chamber 37. The chamber 37 of the system of FIGS. 10 and 11 differs from FIGS. 8 and 9 in that the chamber 37 of FIGS. 10 and 11 includes a step 38 in channel 10 that acts to fill the chamber 37. That is, chamber 37 of FIGS. 10 and 11 is formed within the first section 23 of the system or channel 10 by the gate 36, the channel sidewalls 6, the channel bottom 4 and the step 38. Fluid, including any bore waves, flows over step 38 into the chamber 37 to fill the chamber 37. The depth $d_3$ of the fluid in the chamber 37 is filled at a higher level than the depth $d_1$ of cultivation fluid 3 in the second section 24 of the system or channel, which is downstream of the bore wave generator 30. The gate 36 can be raised or lowered (as illustrated by the up and down arrows in FIG. 11) to collect fluid in the chamber 37 or to release fluid from the chamber 37 to the rest of the channel (i.e., to the second section 24). When the gate 36 is raised, the fluid in the chamber 37 rapidly enters the second section of the channel 10, forming an undulated bore wave with an initial wave 1, followed by a second undulation 2.

Figure 12:
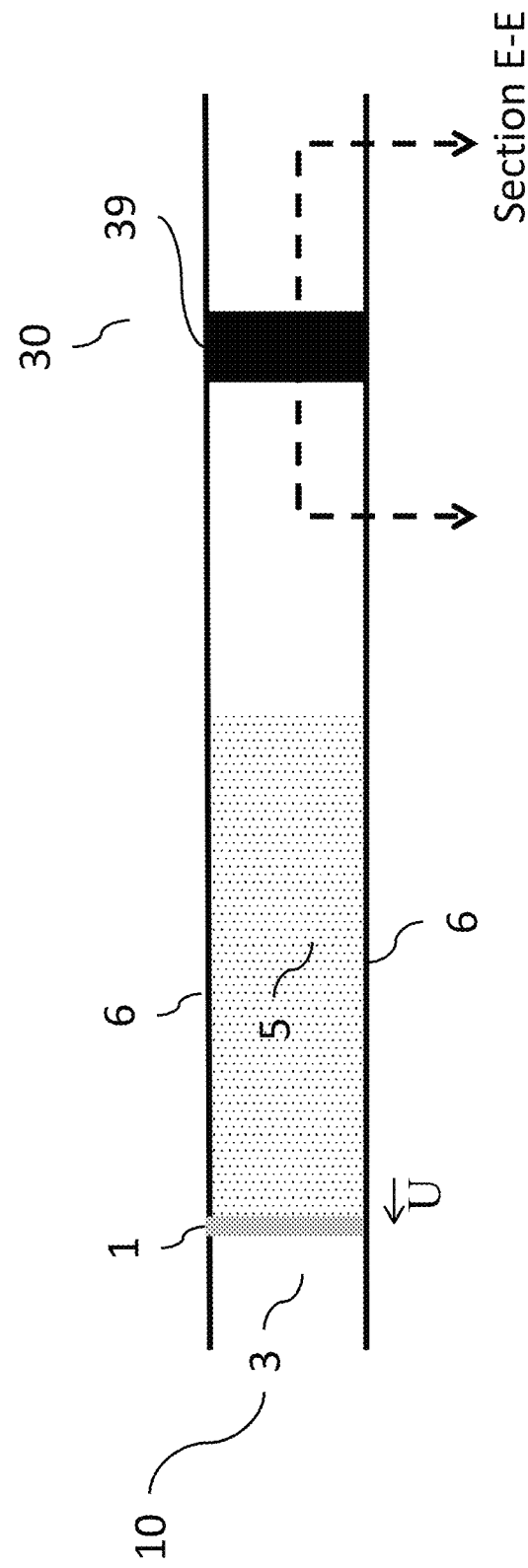
FIG. 12 is a plan view illustrating bore or translating jump waves travelling in an algae cultivation system having a translating hydraulic jump wave generator with a moveable barrier according to one embodiment of the present disclosure.
Figure 13:
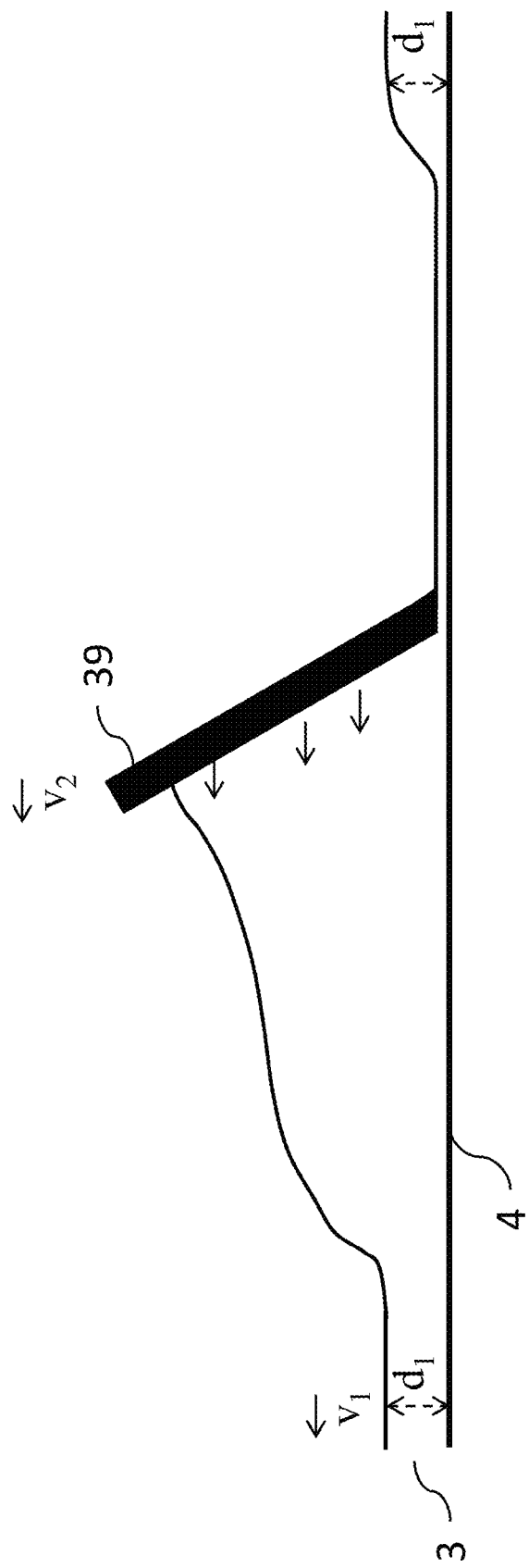
FIG. 13 is a cross-sectional view taken along lines E-E of FIG. 12.

FIGS. 12 and 13 illustrate another non-limiting embodiment of an algae cultivation system of the present disclosure in which the translating hydraulic jump wave generator includes a moveable barrier 39. FIG. 12 illustrates a plan view of the system, while FIG. 12 is a cross-sectional view. The system of FIG. 12 includes a channel section 10 that contains the algae cultivation fluid, and a bore or translating hydraulic wave generator 30 having a barrier 39. Barrier 39 is translatable parallel to a bottom 4 of the channel 10 at a velocity $v_2$ that is greater than the velocity $v_1$ of the downstream cultivation fluid 3. The cultivation fluid in front of the wave generator 30 is accelerated and increases in depth to generate a bore wave 1 that travels down the channel 10 away from the wave generator 30. The velocity $v_1$ of the downstream cultivation fluid 3 can be away from or toward the wave generator 30 depending upon the slope of the channel bottom 4. If the downstream cultivation fluid 3 is moving toward the barrier 39, then the velocity $v_1$ of the fluid is negative, so the velocity $v_2$ of the barrier 39 will be greater than the velocity $v_1$ of the fluid 3, even if the barrier 39 simply drops into place and the barrier velocity $v_2$ is zero.

If the barrier velocity $v_2$ is zero, and if the channel 10 slopes down toward the barrier 39 from both directions, two waves can be generated simultaneously by dropping the barrier 39 into place causing cultivation fluid to build up on the barrier 39 such that the bore wave 1 is formed in each direction.

Figure 14:
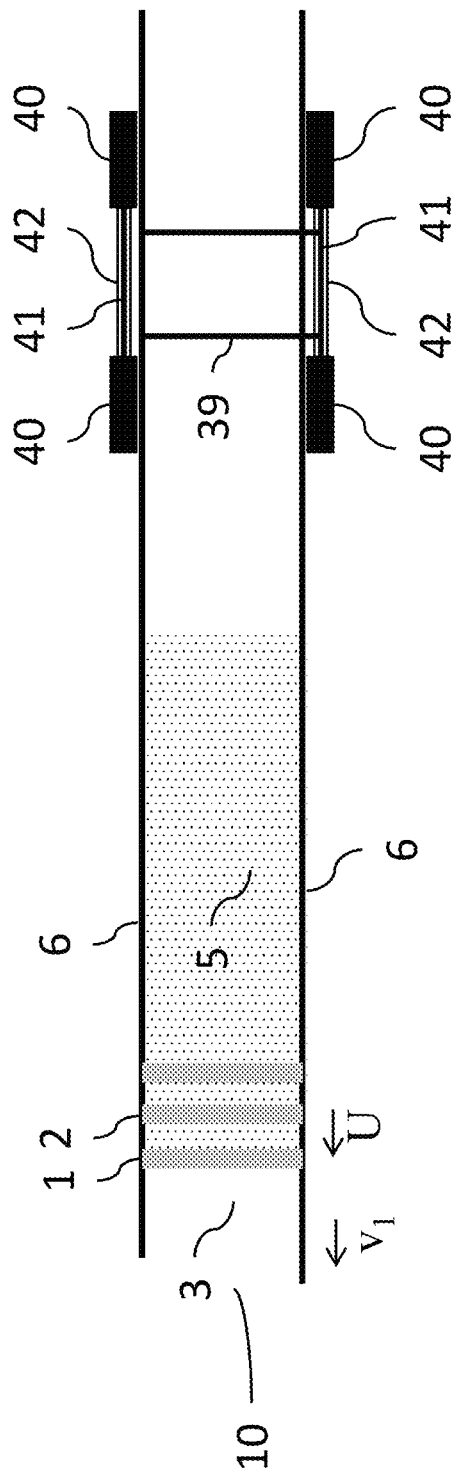
FIG. 14 is a plan view illustrating an undulated bore or translating jump waves travelling in an algae cultivation system having a translating hydraulic jump wave generator with a moveable barrier according to another embodiment of the present disclosure.
Figure 15:
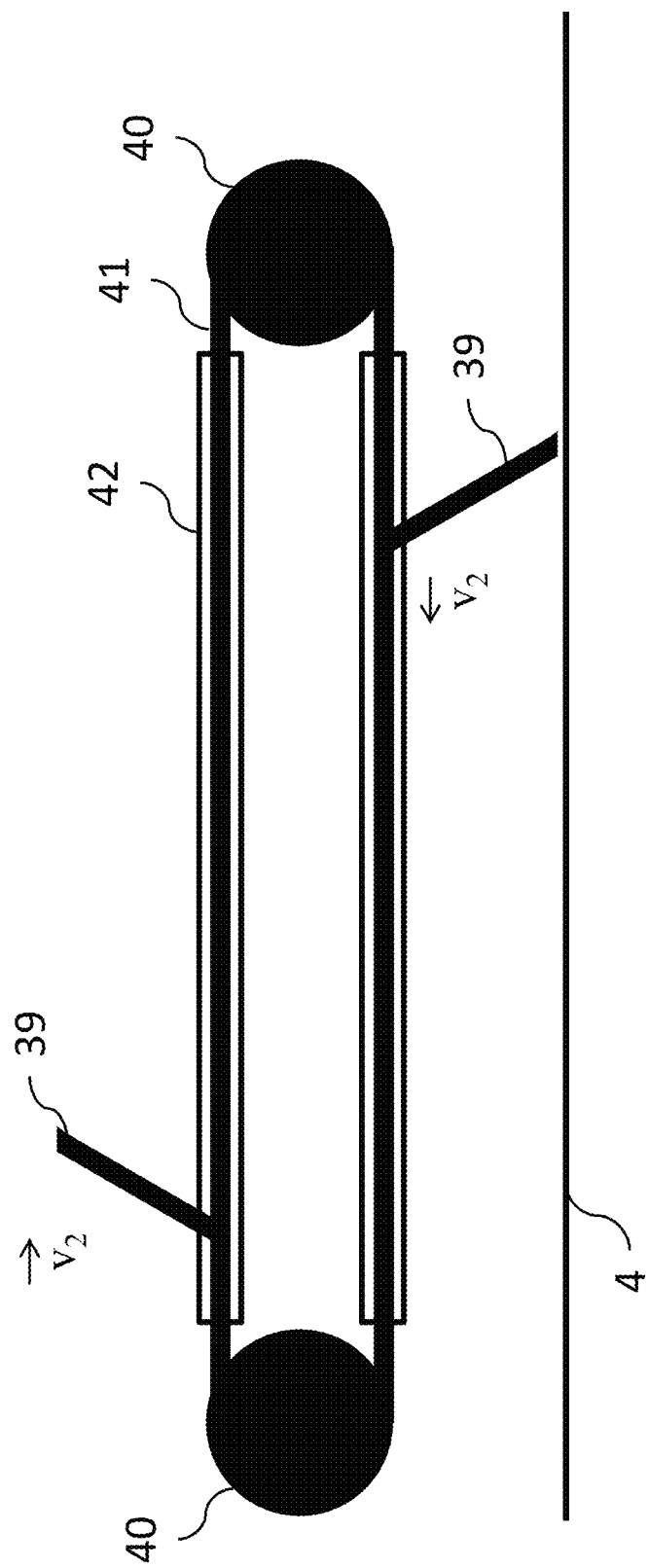
FIG. 15 is side view of the algae cultivation system of FIG. 14.

After a bore wave 1 is generated, the barrier 39 can be lifted up and re-positioned so that it is ready to generate another wave. During this time, the cultivation fluid will refill the channel 10 upstream of the barrier 39 by gravity-induced flow. Barrier 39 can be moved, lifted or repositioned using any suitable mechanism or technique. In one example, barrier 39 is moved via a first set of linear actuators that move the barrier 39 in a forward and backward stroke, and a second set of linear actuators that move the barrier 39 down into the fluid during the forward stroke and lift the barrier 39 out of the fluid during the return stroke. In another example, the barrier 39 travels in a guide 42 and is attached to a chain 41 that moves in a generally elliptical or oval motion driven by a motor and sprockets 40, as illustrated by FIGS. 14 and 15.

Figure 16:
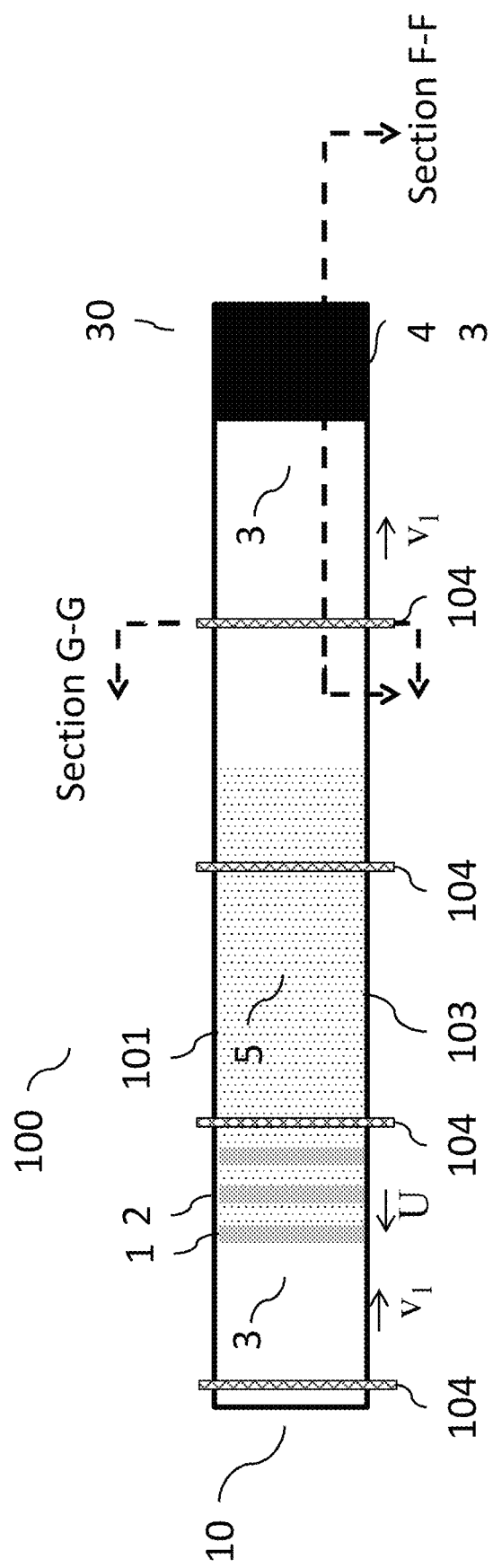
FIG. 16 is a plan view illustrating an undulated bore or translating jump wave travelling in an algae cultivation system having a hinged plate translating hydraulic wave generator according to one embodiment of the present disclosure.
Figure 17:
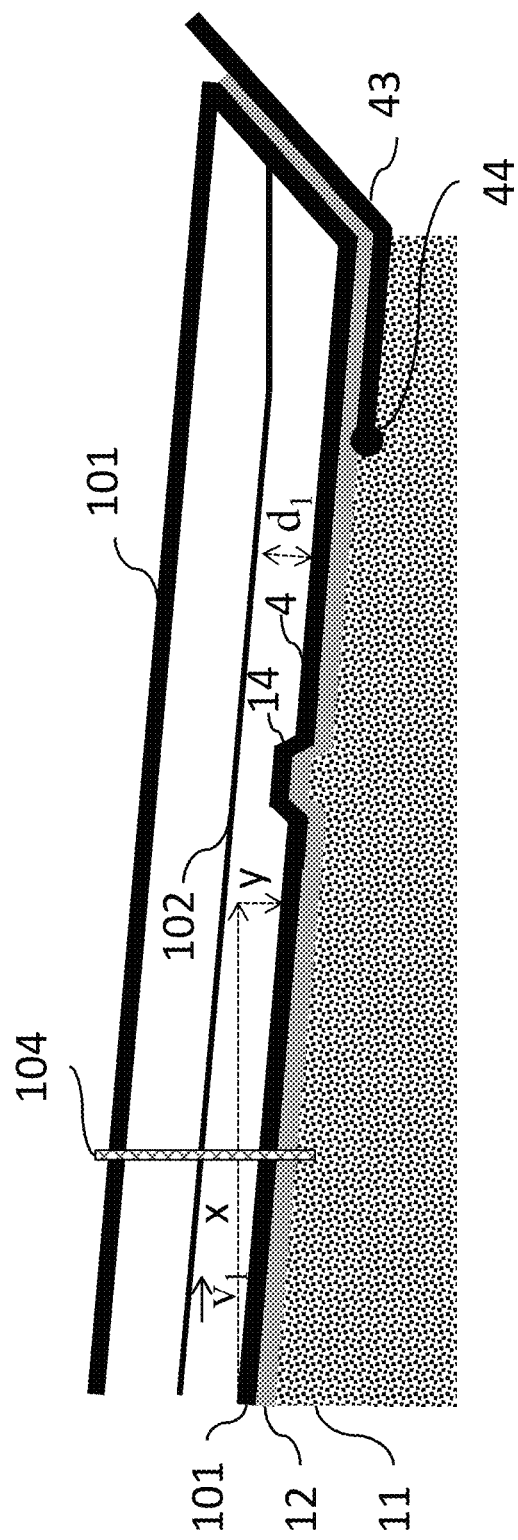
FIG. 17 is a cross-sectional view taken along lines F-F of FIG. 16.
Figure 18:
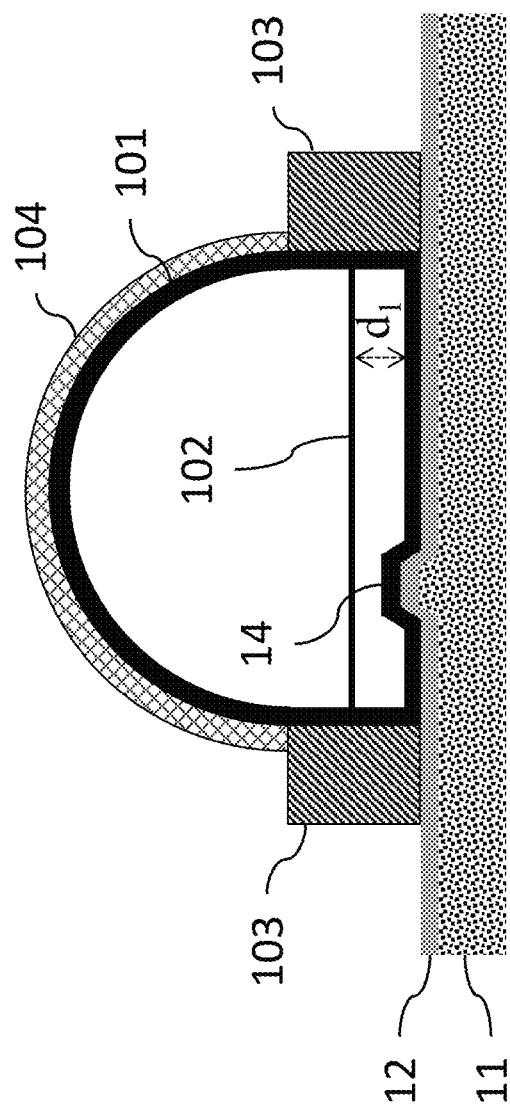
FIG. 18 is a cross-sectional view taken along lines G-G of FIG. 16.

FIGS. 16, 17 and 18 illustrate a bore or translating jump wave travelling in an algae cultivation system having a wave generator with a hinged plate 43 according to another embodiment of the present disclosure. Here, the algae cultivation system is a closed photobioreactor having a channel 10 that contains the algae cultivation fluid. The system of FIGS. 16, 17 and 18 includes a wave generator 30 and flexible walls 101, which can comprise one or more plastic sheets that are transparent to light and sealed to form a horizontal bag. The bag is placed on an underlayment 12, which is on the ground 11 having a graded slope is defined by y/x, where y is vertical and x is horizontal. The grade of the slope in the illustrated system is such that the cultivation fluid 3 flows to an end of the channel 10 where the wave generator 30 is located. The plastic bag can be pressurized to keep the upper section of the bag above the liquid surface so that a gas-liquid interface 102 is maintained along the length of the channel 10. The wave generator 30 creates bore waves 1 that travel in a direction opposite to the direction the cultivation fluid 3 flows. The wave generator 30 includes a plate 43 that can be raised and lowered on a pivot point 44. FIG. 17 illustrates plate 43 in the lowered position where cultivation fluid accumulates as a result of the plate 43 being located at the low end of the channel 10. To generate the bore wave 1, the plate 43 is raised, which causes the accumulated cultivation fluid to flow rapidly up the channel 10, creating the bore wave 1. The walls 101 defined by the flexible plastic bag are held in place by the ground 11 and side supports 103. Side supports 103 can be moved generally horizontally inwardly to create a narrower channel 10 or horizontally outwardly to create a wider channel 10. The plastic bag will maintain a generally oval shaped dome above the channel 10 because the bag is pressurized sufficiently to support the upper section of the plastic sheet 101. Tie-downs 104 can be spaced along the length of the photobioreactor channel 10 so that the shape is maintained with a slightly pressurized interior.

While the above figures illustrate specific embodiments of the present disclosure, translating hydraulic or bore wave fluid transport is applicable to a variety of different cultivation systems and methods and in many combinations. Examples of alternative cultivation systems of the present disclosure include systems with channels that are not straight, combinations of photobioreactors and open systems, systems that include covered raceways, systems with intermediate wave generation devices along the length of the channels, and systems with wave reflecting walls. While most of the figures herein illustrate one or two wave generators, additional wave generators can be positioned throughout the cultivation systems as needed to achieve the desired operational depth and mixing. Furthermore, cultivation systems with multiple wave generators may include more than one type of wave generator.

It should be appreciated from the foregoing that the present disclosure includes an algae cultivation method, which includes generating a translating hydraulic jump wave having a Froude number greater than 1 across a gas-liquid interface of an algae cultivation fluid contained in an algae cultivation system. The algae cultivation method of can further include preparing an algae slurry in an aqueous cultivation fluid to create the algae cultivation fluid, and introducing the algae cultivation fluid into the algae cultivation system.

It should further be appreciated that each of the embodiments described herein including the methods can operate with one or more controllers, which can be programmed or configured to operate with any of the wave generators, the side supports, the moveable barriers, or the plates and/or any other system components to perform various functions of the algae cultivation systems and methods, including generating the bore waves, or moving the plates, the side supports or the barriers. In an embodiment, the one or more controllers can include at least one processor and at least one memory device which stores instructions, which when executed by the at least one processor, cause the at least one processor to operate with one or more of the wave generators, the barriers, or the plates to perform said operations of the algae cultivation systems and methods. It should additionally be appreciated that certain embodiments can include at least one input device and/or the at least one display device, and the one or more controllers can be programmed or configured to operate with the at least at least one input device and/or the at least one display device.

Various example embodiments, examples and/or simulations of the systems and methods of the present disclosure are discussed below.

EXAMPLE 1

*Chlorella* sp. cultivated in a conventional deep algae cultivation system or raceway at about 25 cm deep and 15 cm/s velocity attains a productivity of about 8 to 9 grams per meter squared per day ($g/m^2d$). *Chlorella* sp. was cultivated in a half-acre, lined-earthen, sloped cultivation system according to the embodiment illustrated in FIGS. 4-6 above, but without the use of bore waves or a wave generator. A productivity of 13 to 14 $g/m^2d$ was attained under the operational conditions of a slope of about 0.06%, a culture depth of 10 cm, and an average culture circulation velocity of 30 cm/s. A bore wave generator was added to the half-acre, lined-earthen, sloped cultivation system, and *Chlorella* sp. was cultivated in the cultivation system at a very shallow depth with bore waves. A productivity of 23 to 25 $g/m^2d$ was attained under the operational conditions of a slope of about 0.06%, a culture depth of 4 cm, and culture circulation via a variable flow pump bore wave generator. Thus, the addition of a bore wave generator to improve mixing and enable very shallow operation increased the productivity by 78% over a shallow sloped raceway and 182% over a conventional raceway.

EXAMPLE 2

Typical algae cultivation systems rely upon creating good mixing through turbulence from the cultivation fluid velocity. The degree of turbulence correlates with the Reynold's number, where the Reynolds number is defined as the dvp/μ, where d is the depth of the cultivation media, v is the velocity, p is the density, and μ is the viscosity. If the Reynold's number is greater than 12,500, then the flow is turbulent. The higher the Reynold's number, the greater the degree of turbulence. A conventional algae system operating at a depth of 25 cm with a velocity of 12 cm/s has a Reynold's number of about 30,000. Table 1 below provides a summary of the required slope and approximate energy loss to attain the level of mixing in a conventional system, a shallow system, a very shallow system, and a very shallow bore wave mixed system. Comparing very shallow cultivation system with and without the addition of a bore wave generator reveals that the bore wave system provides a forty-fold reduction in the energy use. Comparing the very shallow system with the shallow sloped system reveals that adding the bore wave generator provides a two-fold reduction in energy use. Considering the results in Example 1 above, a 78% improvement in productivity can be attained simultaneously with the two-fold reduction in energy use.

TABLE 1

Slope and energy requirements for various cultivation systems with a Reynold's number of 30,000

| Cultivation System | Depth (cm) | Estimated Slope | Estimated energy loss (W/m2) |
|---|---|---|---|
| Conventional | 25 | .004% | 0.004 |
| Shallow sloped | 10 | 0.06% | 0.1 |
| Very shallow sloped | 4 | 1.3% | 2 |
| Very shallow sloped with a bore wave generator | 4 | 0.06% | 0.05 |

EXAMPLE 3

As discussed above, one embodiment of the algae cultivation systems and methods herein include a translating hydraulic jump wave with a Froude number of 1.3 or greater. Neglecting frictional losses across the translating hydraulic jump, the ratio of depths before and after a translating hydraulic jump is 1.4:1 for a Froude number of 1.3. Table 2 below provides wave velocity relative to the cultivation fluid velocity as a function of depth and the ratio of the volumetric flow in the wave to the volumetric flow of the cultivation media as a function of the cultivation depth and cultivation velocity assuming the wave is 40% of the baseline depth, the Froude number is 1.3, and the cultivation media is traveling in the same direction as the wave. If a variable flow pump wave generator is used to produce the wave, then the pump would need a minimum turn-down ratio at least equal to the ratio of the volumetric flows presented in Table 2. Thus, the variable flow rate pump turndown ratio needs to be at least 1.5:1 and in certain embodiments about 3:1. The lowest volumetric flux in Table 2 corresponds to a cultivation depth of 1 cm and a cultivation velocity of 5 cm/s. Under these conditions, the wave velocity is 46 cm/s, the wave height is 0.4 cm.

TABLE 2

Volumetric ratio of wave to cultivation media assuming wave height that is 40% above the cultivation depth and a Froude number of 1.3

| Cultivation Depth (cm) | Wave velocity relative to the cultivation velocity (cm/s) | Cultivation velocity (cm/s) | | |
|---|---|---|---|---|
| | | 15 | 10 | 5 |
| 1 | 41 | 1.5 | 2.1 | 3.7 |
| 2 | 58 | 2.0 | 2.7 | 5.1 |
| 3 | 70 | 2.3 | 3.3 | 6.1 |
| 4 | 81 | 2.6 | 3.7 | 7.0 |
| 5 | 91 | 2.9 | 4.1 | 7.8 |
| 6 | 100 | 3.1 | 4.4 | 8.5 |
| 7 | 1.08 | 3.3 | 4.8 | 9.1 |

EXAMPLE 4

A cultivation system sloped down toward a wave generator instead of down away from a wave generator has a cultivation media flow that is in the opposite direction as the wave. If the system slope is 0.1% and the cultivation depth is 1.5 cm, then the cultivation fluid velocity will be approximately −11 cm/s. A wave with a Froude number of 1.3 and a cultivation depth of 1.5 cm, has a translating hydraulic jump velocity relative to the cultivation fluid of 50 cm/s. Since the translating hydraulic jump velocity minus the cultivation fluid velocity is 50 cm/s, the translating hydraulic jump velocity relative to a fixed point in the of the cultivation system is 39 cm/s.

EXAMPLE 5

A wave generator was built by installing a gate in front of a paddlewheel in a channel in a level cultivation system as illustrated in FIGS. 8 and 9 above. The gate could be lowered and raised with a linear actuator to release the bore waves. The cultivation depth was 2.5 cm. The fluid level in the chamber created between the gate, the paddlewheel, and the channel sidewalls was increased through operation of the paddlewheel. The wave was released by raising the gate when the fluid height reached 7.5 cm. This created a translating hydraulic jump or bore wave with a velocity of 100 cm/s and a depth of 5 cm. The wave induced a cultivation velocity of approximately 14 cm/s in the cultivation media between the waves. The cultivation velocity was in the same the direction of the wave, so the Froude number of bore wave attained with these operating conditions was approximately 1.7.

We claim:
1. An algae cultivation system comprising:
   a wave generator in a fixed location in the system, the wave generator configured to generate a translating hydraulic jump wave that travels across a gas-liquid interface of an algae cultivation fluid contained in the algae cultivation system in order to provide both circulation and mixing of the algae cultivation fluid, the translating hydraulic jump wave having a Froude number greater than 1, wherein the algae cultivation system is one of an open or covered raceway or a closed horizontal photobioreactor with an air-gap between the algae cultivation fluid and a top of the photobioreactor.
2. The algae cultivation system of claim 1, wherein the wave generator is configured to generate the translating hydraulic jump wave with the Froude number greater than 1.3.

3. The algae cultivation system of claim 1, wherein the wave generator is configured to generate the translating hydraulic jump wave with a ratio of wave depth to algae cultivation fluid depth of greater than 1.15.

4. The algae cultivation system of claim 3, wherein the ratio of the translating hydraulic jump wave depth to the algae cultivation fluid depth is at least 1.4.

5. The algae cultivation system of claim 1, wherein the wave generator is configured to generate the translating hydraulic jump wave with a velocity of greater than 40 cm/s relative to a velocity of the algae cultivation fluid.

6. The algae cultivation system of claim 1, wherein the wave generator is configured to generate the translating hydraulic wave with a velocity of greater than 70 cm/s relative to a velocity of the algae cultivation fluid.

7. The algae cultivation system of claim 1, wherein the raceway includes one of (i) an earthen bottom, or (ii) an earthen bottom and a plastic liner covering the earthen bottom.

8. The algae cultivation system of claim 1, wherein the raceway includes at least one channel having a slope between −0.5% and 0.5%.

9. The algae cultivation system of claim 1, wherein the raceway includes at least one channel with a slope between −0.1% and 0.1%.

10. The algae cultivation system of claim 1, wherein the raceway or closed photobioreactor includes at least one channel with a light permeable cover.

11. The algae cultivation system of claim 1, wherein the raceway or closed photobioreactor includes at least one channel with a channel bottom, the at least one channel bottom (i) sloped upward from the wave generator, or (ii) sloped downward from the wave generator.

12. The algae cultivation system of claim 1, wherein (i) the raceway or closed photobioreactor includes a first channel and a second channel, and (ii) the wave generator includes a first wave generator and a second wave generator, the first wave generator positioned at an entrance of the first channel and the second wave generator positioned at an entrance of the second channel.

13. The algae cultivation system of claim 12, wherein the first channel is sloped in an opposite direction of the second channel.

14. The algae cultivation system of claim 1, wherein the closed photobioreactor includes (i) at least one channel having a width and a flexible wall enclosing the gas-liquid interface, and (ii) horizontally adjustable side barriers constructed and arranged such that when the adjustable side barriers move horizontally, the width of the at least one channel changes, thereby changing a cultivation area of the closed photobioreactor.

15. The algae cultivation system of claim 1, wherein the raceway or the closed photobioreactor includes an algae cultivation fluid depth of 0.5 to 6.5 cm.

16. The algae cultivation system of claim 1, wherein the wave generator includes a fluid pump having a variable flow control mechanism.

17. The algae cultivation system of claim 16, wherein the variable flow control mechanism is configured to drive between a low volumetric flow and a high volumetric flow, the low volumetric flow 50% or lower than the high volumetric flow.

18. The algae cultivation system of claim 16, wherein the variable flow control mechanism includes a variable speed drive.

19. The algae cultivation system of claim 16, wherein the fluid pump includes one of (i) a propeller pump, (ii) an Archimedes screw pump, or (iii) a paddle wheel.

20. The algae cultivation system of claim 1, wherein (i) the raceway or the closed photobioreactor includes a first section, a second section, a bottom and sidewalls, and (ii) the wave generator includes a chamber formed in the first section of the raceway or closed photobioreactor, and wherein (iii) the chamber is defined by a gate, the bottom and the sidewalls, the chamber configured to contain the algae cultivation fluid at a height greater than a height of the algae cultivation fluid in at least a portion of the second section of the raceway or closed photobioreactor, and (iv) the gate is moveable between (a) an algae cultivation fluid collecting position in which the algae cultivation fluid is collected in the chamber and (b) an algae cultivation fluid release position in which the algae cultivation fluid is released from the chamber to the second section of the channel.

21. The algae cultivation system of claim 20, wherein one of the sidewalls of the raceway or closed photobioreactor that defines the chamber includes a step down.

22. The algae cultivation system of claim 21, wherein the algae cultivation fluid height upstream of the step down is equal to or greater than the algae cultivation fluid height in the chamber.

23. The algae cultivation system of claim 20, wherein the chamber is structured to contain the algae cultivation fluid at a depth that is least 1.5 times the depth of the algae cultivation fluid in said at least a portion of the second section of the raceway or closed photobioreactor.

24. The algae cultivation system of claim 20, wherein the wave generator includes a fluid pump and the chamber is further defined by the fluid pump, and wherein the fluid pump includes an outlet that communicates fluidly with the chamber.

25. The algae cultivation system of claim 24, wherein the fluid pump includes one of (i) a propeller pump, (ii) an Archimedes screw pump, or (iii) a paddlewheel.

26. The algae cultivation system of claim 1, wherein the wave generator includes a moveable barrier translatable relative to the algae cultivation fluid, the moveable barrier configured to accelerate the algae cultivation fluid within the algae cultivation system.

27. The algae cultivation system of claim 1, the raceway or closed photobioreactor including a bottom, and wherein the wave generator includes a movable plate positioned on the bottom of the raceway or the closed photobioreactor, the moveable plate moveable between (i) a lowered position in which the algae cultivation fluid accumulates, and (ii) a raised position in which the accumulated algae cultivation fluid flows upstream to generate the translating hydraulic jump wave.

28. The algae cultivation system of claim 27, wherein the movable plate forms a portion of the bottom of the raceway or closed photobioreactor.

29. The algae cultivation system of claim 1, wherein the wave generator includes a plurality of wave generators positioned at different locations in the raceway or closed photobioreactor.

30. The algae cultivation system of claim 1, which includes (i) a first channel having a substantially straight outer sidewall and a substantially straight inner sidewall, (ii) a second channel having a substantially straight outer sidewall and substantially straight inner sidewall, and (iii) a bend fluidly coupling the first channel to the second channel, wherein the bend includes (a) a first angled wall extending from the substantially straight outer sidewall of the first channel at an angle of at least 135 degrees relative to the substantially straight outer sidewall of the first channel and (b) a second angled wall extending from the substantially outer sidewall of the second channel at an angle of at least 135 degrees relative to the substantially straight outer sidewall of the second channel.

31. The algae cultivation system of claim 30, wherein the bend includes an end wall connecting the first angled wall to the second angled wall, the end wall substantially perpendicular to the inner and outer sidewalls of the first and second channels.

32. The algae cultivation system of claim 30, wherein the bend is located at one end of the first and second channels, and wherein the wave generator is located at another end of the first and second channels that fluidly couples the first and second channels.

33. An algae cultivation method comprising: generating a translating hydraulic jump wave with a Froude number greater than 1 that travels across a gas-liquid interface of an algae cultivation fluid contained in an algae cultivation system in order to provide both circulation and mixing of the algae cultivation fluid, the hydraulic jump wave generated by a wave generator in a fixed location in the algae cultivation system, wherein the algae cultivation system is one of an open or covered raceway or a closed horizontal photobioreactor with an air-gap between the algae cultivation fluid and a top of the photobioreactor.

34. The algae cultivation method of claim 33, wherein the translating hydraulic jump wave includes the Froude number greater than 1.3.

35. The algae cultivation method of claim 33, wherein the translating hydraulic jump wave includes a ratio of wave depth to algae cultivation fluid depth of greater than 1.15.

36. The algae cultivation method of claim 33, wherein the translating hydraulic jump wave includes a ratio of wave depth to algae cultivation fluid depth of at least 1.4.

37. The algae cultivation method of claim 33, wherein the translating hydraulic jump wave includes a velocity of greater than 40 cm/s relative to a velocity of the algae cultivation fluid.

38. The algae cultivation method of claim 33, wherein the translating hydraulic jump wave includes a velocity of greater than 70 cm/s relative to a velocity of the algae cultivation fluid.

39. The algae cultivation method of claim 33, which includes maintaining a depth of 0.5 cm to 6.5 cm for the algae cultivation fluid in at least a portion of the algae cultivation system.

40. The algae cultivation method of claim 33, wherein the raceway includes one of (i) an earthen bottom, or (ii) an earthen bottom with a plastic liner covering the earthen bottom.

41. The algae cultivation method of claim 33, wherein the raceway includes at least one channel with a slope between −0.5% and 0.5%.

42. The algae cultivation method of claim 33, wherein the raceway includes at least one channel with a slope between −0.1% and 0.1%.

43. The algae cultivation method of claim 33, wherein the algae cultivation system includes at least one channel with a light permeable cover.

44. The algae cultivation method of claim 33, wherein the closed photobioreactor includes at least one channel having a sloped bottom.

45. The algae cultivation method of claim 44, wherein the sloped channel is upward sloped or downward sloped, and which includes generating the translating hydraulic jump wave so that the wave moves up the upward sloped channel or moves down the downward sloped channel.

46. The algae cultivation method of claim 33, which includes: preparing an algae slurry in an aqueous cultivation fluid to create the algae cultivation fluid; and introducing the algae cultivation fluid into the algae cultivation system.

47. The algae cultivation method of claim 33, which includes:
 introducing additional algae cultivation fluid to the closed photobioreactor; and increasing a cultivation area of the closed photobioreactor as the algae volume in the closed photobioreactor increases.

48. The algae cultivation method of claim 33, which includes: removing algae slurry from the algae cultivation system; and decreasing a cultivation area of the closed photobioreactor as the algae slurry volume in the photobioreactor decreases.

49. The algae cultivation method of claim 33, which includes moving side barriers horizontally to change the width of the closed photobioreactor to thereby change an algae cultivation area of the closed photobioreactor.

50. The algae cultivation method of claim 33, which includes varying a volumetric flow rate of a fluid pump to generate the translating hydraulic jump wave.

51. The algae cultivation method of claim 33, which includes varying a volumetric flow rate of a fluid pump by at least a factor of 2 to generate the translating hydraulic jump wave.

52. The algae cultivation method of claim 51, wherein the fluid pump includes (i) a propeller pump, (ii) an Archimedes screw pump, or a (iii) a paddle wheel.

53. The algae cultivation method of claim 33, wherein the generating of the translating hydraulic jump wave includes:
 filling a chamber in the algae cultivation system with the algae cultivation fluid at a depth that is greater than a depth of the algae cultivation fluid in at least a portion of the cultivation system outside of the chamber; and
 opening a gate that forms a wall of the chamber to release the algae cultivation fluid from the chamber into a portion outside of the algae cultivation system outside the chamber.

54. The algae cultivation method of claim 53, wherein the filling of the chamber includes allowing the algae cultivation fluid to flow over an edge of a step.

55. The algae cultivation method of claim 53, wherein a depth of an algae slurry in the chamber is least 1.5 times the depth of the algae cultivation fluid in the portion of the algae cultivation system outside the chamber.

56. The algae cultivation method of claim 53, wherein the filling of the chamber includes filling the chamber using a fluid pump.

57. The algae cultivation method of claim 56, wherein the fluid pump is one of (i) a propeller pump, (ii) an Archimedes screw pump, or (iii) a paddlewheel.

58. The algae cultivation method of claim 33, wherein the generating of the translating hydraulic jump wave includes moving a barrier within the algae cultivation system to accelerate the algae cultivation fluid.

59. The algae cultivation method of claim 33, wherein the generating of the translating hydraulic jump wave includes pivoting a plate on a bottom of the algae cultivation system.

60. The algae cultivation method of claim 59, wherein the plate forms a portion of the bottom of the algae cultivation system.

61. The algae cultivation method of claim 33, wherein the generating of the translating hydraulic jump wave includes generating multiple translating hydraulic waves at different locations in the algae cultivation system.

62. The algae cultivation method of claim 33, wherein the translating hydraulic jump wave travels through a first substantially straight channel of the algae cultivation system, around a bend of the algae cultivation system, to a second substantially straight channel of the algae cultivation system, without any waves reflecting back to the first channel.

\* \* \* \* \*